United States Patent
Swaile et al.

(10) Patent No.: US 7,905,673 B2
(45) Date of Patent: Mar. 15, 2011

(54) ANTIPERSPIRANT COMPOSITION AND APPLICATOR THEREFOR

(75) Inventors: David Frederick Swaile, Cincinnati, OH (US); Gene Michael Altonen, West Chester, OH (US); Christine Marie Putman, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1628 days.

(21) Appl. No.: 10/990,592

(22) Filed: Nov. 17, 2004

(65) Prior Publication Data

US 2005/0123494 A1    Jun. 9, 2005

Related U.S. Application Data

(60) Provisional application No. 60/520,559, filed on Nov. 17, 2003.

(51) Int. Cl.
  *B43M 11/06*    (2006.01)
(52) U.S. Cl. .................................. 401/265; 222/402.1
(58) Field of Classification Search ................. 401/265, 401/205; 222/402.1, 190, 402.13
  See application file for complete search history.

(56) References Cited

U.S. PATENT DOCUMENTS

| | | | |
|---|---|---|---|
| 2,746,796 A | 5/1956 | St. Germain | |
| 3,685,913 A | 8/1972 | Pass | |
| 3,804,537 A * | 4/1974 | Pass | 401/190 |
| 3,844,448 A * | 10/1974 | Sette | 222/153.12 |
| 4,174,386 A | 11/1979 | Spitzer et al. | |
| 4,344,930 A * | 8/1982 | MacRae et al. | 424/401 |

(Continued)

FOREIGN PATENT DOCUMENTS

GB    1098951    1/1968

(Continued)

OTHER PUBLICATIONS

XP001205529, Root, M.J., "Aerosol Cosmetics", Cosmet. Sci. Technol., 2nd Ed., vol. 2, pp. 417-485, (1972).

*Primary Examiner* — David J Walczak
(74) *Attorney, Agent, or Firm* — Andrew J. Hagerty; Vladimir Vitenberg; Brian M. Bolam

(57) ABSTRACT

An antiperspirant product comprising an antiperspirant composition and an applicator for storing and discharging the antiperspirant composition. The antiperspirant composition comprises an antiperspirant active. The applicator has a longitudinal axis and comprises a release system structured to facilitate discharge of the antiperspirant composition such that the antiperspirant composition discharges as a portion of a foam comprising a dispersion of gas bubbles in a continuous liquid medium comprising the antiperspirant active that is suspended or dissolved therein, and a skin-contacting surface structured to receive and retain the portion of the foam thereon such that the portion of the foam of 0.2 gram is retained on the skin-contacting surface for at least 2 seconds when the applicator is inclined so that the longitudinal axis of the applicator and a gravity force vector form an angle of about 15 degrees therebetween, the skin-contacting surface being configured to apply an effective amount of the foam directly to an underarm area of a consumer.

40 Claims, 7 Drawing Sheets

U.S. PATENT DOCUMENTS

| | | | | |
|---|---|---|---|---|
| 4,636,102 | A | * | 1/1987 | Drake .......................... 401/190 |
| 5,186,364 | A | | 2/1993 | Laszlo |
| 5,352,387 | A | * | 10/1994 | Rahman et al. ................ 510/496 |
| 5,366,665 | A | * | 11/1994 | Cho .............................. 510/152 |
| 5,567,073 | A | | 10/1996 | de Laforcade et al. |
| 5,650,146 | A | * | 7/1997 | Shaw ......................... 424/78.03 |
| 5,813,785 | A | | 9/1998 | Baudin et al. |
| 5,814,309 | A | | 9/1998 | Panitch |
| 5,914,085 | A | | 6/1999 | Zimmerhackel |
| 5,989,531 | A | | 11/1999 | Schamper et al. |
| 6,021,926 | A | * | 2/2000 | Lauwers et al. ........... 222/402.1 |
| 6,494,349 | B1 | | 12/2002 | Thompson et al. |
| 2001/0048841 | A1 | * | 12/2001 | Girardot et al. ............... 401/266 |
| 2006/0286046 | A1 | * | 12/2006 | Haber ............................. 424/59 |
| 2007/0110506 | A1 | * | 5/2007 | Erickson et al. .............. 401/205 |

FOREIGN PATENT DOCUMENTS

| | | |
|---|---|---|
| GB | 1170152 | 11/1969 |
| GB | 2076289 A | 12/1981 |
| GB | 2214891 A | 9/1989 |
| JP | 49037882 | 4/1974 |
| WO | WO 03/053388 A1 | 7/2003 |

* cited by examiner

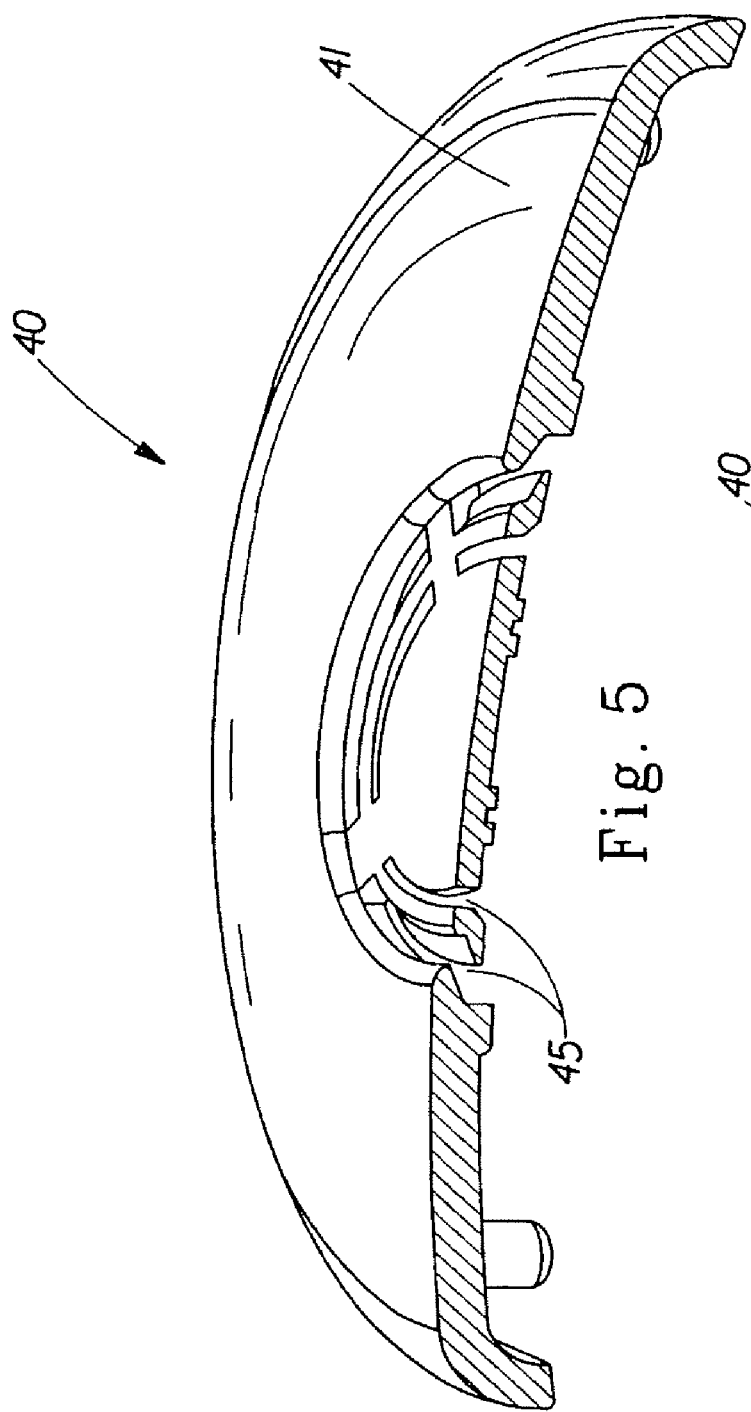
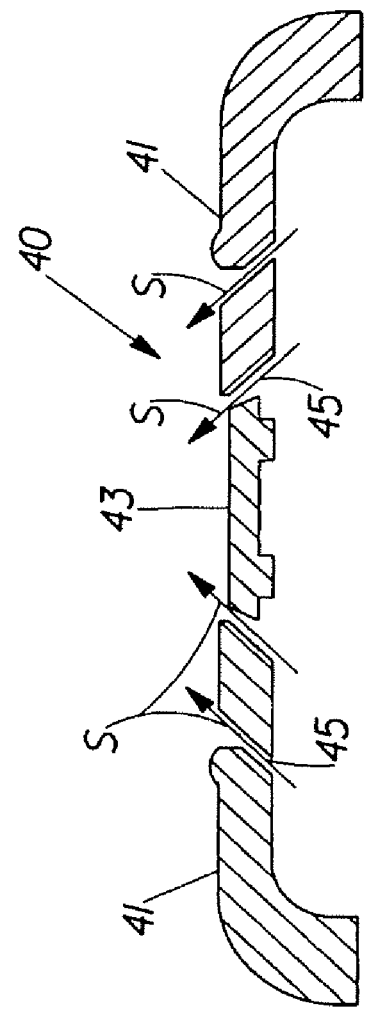
Fig. 5
Fig. 5A

ANTIPERSPIRANT COMPOSITION AND APPLICATOR THEREFOR

CROSS REFERENCE TO RELATED APPLICATION

This application claims the benefit of U.S. Provisional Application Ser. No. 60/520,559, filed Nov. 17, 2003.

FIELD OF THE INVENTION

The present invention relates to antiperspirant products comprising foaming antiperspirant composition in combination with a dispensing applicator, wherein the applicator and the antiperspirant composition are designed to substantially preclude the composition to slide off the applicator and prevents the composition from becoming airborne during dispensing, and is not messy during its use.

BACKGROUND OF THE INVENTION

There are many different antiperspirant formulations known for controlling or inhibiting underarm perspiration and odor. Most of the currently marketed formulations comprise an antiperspirant powder such as an aluminum salt, which is suspended in an anhydrous carrier. Suspension of the active is typically achieved by controlling the viscosity of the anhydrous carrier such that the active is homogenously distributed throughout the product during product dispensing. This viscosity increase can be very high for solid products (more than 3 million centipoises (cps)), high for cream products (25,000 to several million cps) and fairly low for liquid products such as aerosols and roll-ons (300 to 5,000 cps).

One formulation method that can be used to remove the need to suspend the particulate active is to dissolve the active in a carrier liquid. Although any product form can be created using an active dissolved in a carrier liquid, they are most commonly formulated as liquids and delivered as sprays, roll-ons, and water or polar solvent in silicone emulsions. This method removes the need to suspend the active; however many formulations still require control of product viscosity to allow the product to be dispensed in a convenient manner. There are many examples of products based on solubilized active where the carrier liquid comprises a high level of water (more than 20%) that acts as the solvent for the aluminum salt antiperspirant active. Generally, these products are sold as emulsions, either oil in water or water in oil and range in viscosity from about 100 cps for a roll-on to 100,000 cps for water-in-silicone emulsion gel product. The required viscosity of the product is typically dependent on the type of package that is used to deliver the product but can also be driven by need the prevent phase separation of the emulsion. Anhydrous products based on solubilized actives are less common in the market place but there are several examples disclosed in the prior art. U.S. Pat. No. 5,814,309 (Sep. 29, 1998, Panitch) discloses a transparent aerosol composition comprising an active antiperspirant salt, a carrier, and a hydrocarbon gas propellant.

Low-viscosity (less than 100 cps) anhydrous liquid products can be formulated as sprays but as such are prohibited from using high efficacy aluminum and zirconium based antiperspirant actives in many markets due concerns over the inhalation. Roll-on products can use aluminum and zirconium actives and can be formulated to have a wide variety of viscosities; however, the roll-on products lack the ability to control product dose independently of spreading the product, i.e., the roll-on product continues to dose as long as the package is being rubbed on the skin. Anhydrous emulsions are also known in the art. U.S. Pat. No. 5,989,531 (Nov. 23, 1999, Schamper et al.) discloses liquid composition, which provides a drier feel and reduces leakage when used with certain types of applicators. However, the formulations that require a high polar solvent phase to silicone emollient phase ratio have a high viscosity—higher than 2000 centipoises—that is undesirable because it may be difficult to spread over the underarm skin.

Another way to deliver liquid products in cosmetically acceptable manner is to convert the liquid to foam prior to application. The conversion of the composition into foam causes the increase of apparent viscosity of the foam composition without increasing its true viscosity. This allows a foam product having a relatively low true viscosity but a relatively high apparent viscosity to be spread easily in the underarm area. Moreover, the gas or air entrapped in the foam is believed to create a drier feel during application.

Pressurized foam products are typically packaged in metal cans, or glass or plastic containers. These pressurized containers are typically fitted with a valve to close the package and release the pressurized product when actuated by the user. U.S. Pat. No. 2,746,796 (May 22, 1956, Germain) discloses a metering valve aerosol bottle. U.S. Pat. No. 6,494,349 (Dec. 17, 2002, Thompson, et al.) discloses a hand-held product dispenser comprising a valve mechanism for adjusted "throttled" delivery of the product. U.S. Pat. No. 3,685,913 (Aug. 22, 1972, Pass) discloses an applicator for spreading of shave cream lather, depilatories, unguents and the like substances. UK Patent Application GB 2214891A discloses a container for pressurized material. U.S. Pat. No. 5,813,785 (Sep. 29, 1998, Baudin et al.) discloses a device for packaging, dispensing and application of a product packaged in a liquid form and dispensed in the form of foam or gel. U.S. Pat. No. 5,567,073 (Oct. 22, 1996, de Laforcade) discloses an applicator device for liquid, including a container and a dispenser head connected to the container via a dispenser cap. GB 1098951 discloses a collapsible foam aerosol antiperspirant. GB 1170152 discloses foam antiperspirant products. JP 49037882 discloses foaming aerosol compositions containing alcohols, cellulose and/or vinyl-type polymers, organic solvents, and propellants. U.S. Pat. No. 5,914,085 (Jun. 22, 1999, Zimmerhackel) discloses an actuator for an aerosol container for dispensing foam.

The disclosed in the prior art dispensing actuators to convert a liquid product into foam and those that integrate an application surface into the dispensing orifice can provide an advantage for products such as carpet cleaners and shave foams in that they avoid the need for the user to touch the product with a hand during application or use a secondary application device such as a brush, a towel, or an applicator pad. Further, these packages that provide an integrated application surface can be adapted to include several types of mechanisms to actuate the valve to cause product to flow to the application surface. While these applicator designs are useful for the application of many foam products, they fail to address several important needs for an antiperspirant foam product. For example, these applicators do not address the need to prevent the foam from sliding off the applicator, they do not address the need to prevent the foam from becoming airborne as it is dispensed, and they do not address the need to rub a very thin layer of the product onto the skin.

Known foaming antiperspirant compositions are designed to be applied by hand to the underarm. Now, it has been discovered that the use of an integral applicator for a foaming antiperspirant is desirable since it avoids the need for the user to touch the product prior to application, thus being less messy and more convenient. Moreover, there are several important design elements of an integral applicator for a foaming antiperspirant that must be considered. First, it is important that the dispensed product not slide off the applicator prior to application to the underarm. Second, it is important that the product not become airborne upon dispensing so as to prevent the product being inhaled be the user, creating a mess, or possibly damaging a surrounding surface (e.g. staining, discoloring). Third, it is important that the applicator spread the product out broadly distributed on the applicator surface so as to maximize coverage during application, while at the same time ensuring the foam does not run off the sides of the applicator. The need to avoid dispensing too much product onto the application surface (commonly referred to as "overdosing") is also important; if too much product is dispensed, the product is more prone to drip, slide, or fall off the application surface, which causes messiness.

The foaming antiperspirant products that were designed to be initially applied by dispensing the foam onto the consumer hand (like most shaving creams) and then rubbed onto the underarm skin are less desirable. This two-step process leaves some of the sticky antiperspirant active on the hand and causes overdosing of the product, both of which are undesirable side effects of the two-step process.

The present invention is directed to an antiperspirant product comprising a combination of an antiperspirant composition and an applicator therefor, having a specific set of characteristics that would allow a consumer to apply a small predetermined amount of an antiperspirant composition in a single-step process from the applicator directly to the underarm area while avoiding overdosing of the product, its sliding off the applicator and accompanying messiness, minimizing the potential for the composition to become airborne while maximizing the composition coverage area during its application to the skin.

In the case of a clear foam antiperspirant composition, it is desirable to allow the user to see the clear product. The user is better able to understand that the foam product will go on clear, since while the foam is opaque when dispensed onto the application surface, it returns to a clear fluid when rubbed against the underarm. Thus, it is desirable to package a clear antiperspirant foam product in a clear container, such as a clear plastic container.

SUMMARY OF THE INVENTION

An antiperspirant product of the present invention comprises, in combination: (a) an antiperspirant composition comprising an antiperspirant active; and (b) an applicator for storing and discharging the antiperspirant composition. The applicator has a longitudinal axis and comprises (i) a release system structured to facilitate discharge of the antiperspirant composition such that the antiperspirant composition discharges as a portion of a foam comprising a dispersion of gas bubbles in a continuous liquid medium comprising the antiperspirant active that is suspended or dissolved therein, and (ii) a skin-contacting surface structured to receive and retain the portion of at least 0.2 gram, and more specifically at least 0.5 gram, of the foam thereon such that the portion of the foam is retained on the skin-contacting surface for at least 2 seconds, and more specifically at least 5 seconds, when the applicator is inclined so that the longitudinal axis of the applicator and a gravity force vector form an angle of about 15 degrees, more specifically about 45 degrees, and even more specifically about 90 degrees therebetween, the skin-contacting surface being configured to apply an effective amount of the foam directly to an underarm area of a consumer.

In another aspect, the antiperspirant product of the present invention is structured to prevent the antiperspirant composition from becoming airborne during discharge of the antiperspirant composition onto the skin-contacting surface. When a portion of about 0.5 gram of the antiperspirant composition including no less than 0.001 gram of at least one of an aluminum active or an aluminum-zirconium active or a mixture thereof is discharged onto the skin-contacting surface, less than 0.0004 gram, more specifically less than 0.0002 gram, and even more specifically less than 0.0001 gram, of the at least one of the aluminum active or aluminum-zirconium active or a mixture thereof is transferred to a target having a diameter of 30 millimeters and positioned at a distance of 35 millimeters directly above the skin-contacting surface.

In still another aspect, the present invention is directed to a foam antiperspirant composition which comprises a dispersed gas phase in a continuous liquid medium, the foaming antiperspirant composition comprising: (a) an antiperspirant active, (b) a foam-stabilizing agent, and (c) a propellant, wherein the antiperspirant active and the foam-stabilizing agent are dissolved or dispersed in the continuous liquid medium; and wherein the continuous liquid medium comprises at least 5% of a silicone emollient.

The continuous liquid medium of the composition of the present invention may comprise at least two immiscible liquids. The continuous liquid medium of the foam antiperspirant composition may comprise only miscible liquids. In one embodiment, the continuous liquid medium comprises anhydrous solution. In another embodiment, the continuous liquid medium comprises an aqueous solution. The continuous liquid medium of the foam antiperspirant composition may beneficially comprise a 1,2 diol having at least 4 carbon atoms. The continuous liquid medium of the foam antiperspirant composition may also comprise a silicone emollient having a viscosity of less than about 500 cst. The present composition may utilize the foam-stabilizing agent that is a solid at a room temperature.

BRIEF DESCRIPTION OF THE DRAWINGS

FIG. 5 is a schematic perspective view of a cut-off portion of an exemplary embodiment of the skin-contacting surface, which is structured to direct the flow of the antiperspirant composition away from the periphery of the skin-contacting surface.

FIG. 5A is a schematic cross-sectional view of the exemplary embodiment of the skin-contacting surface shown in FIG. 5.

DETAILED DESCRIPTION OF THE INVENTION

Figure 1:
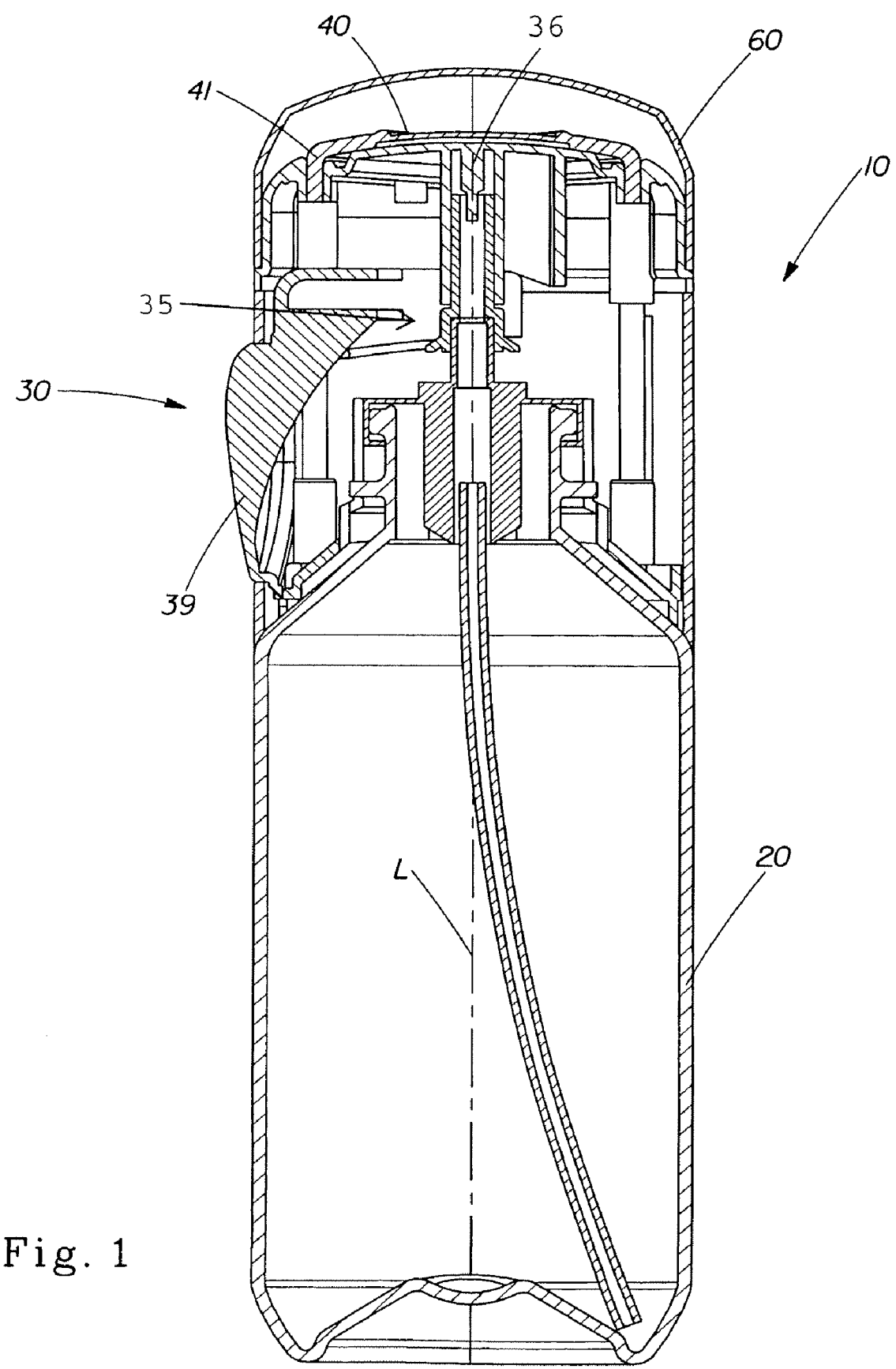
FIG. 1 is a schematic cross-sectional view of an exemplary embodiment of an applicator of the present invention, taken parallel to the applicator's longitudinal axis.

The present invention is directed to an antiperspirant product comprising an antiperspirant composition and an applicator structured to store, dispense, and apply the composition directly to the skin of a user.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

All percentages, parts and ratios as used herein are by weight of the total composition, unless otherwise specified. All such weights as they pertain to listed ingredients are based on the active level and, therefore, do not include polar liquids or by-products that may be included in commercially available materials, unless otherwise specified.

All publications cited herein are hereby incorporated by reference.

The term "plastic" is defined herein as any polymeric material that is capable of being shaped or molded, with or without the application of heat. Usually plastics are a homo-polymer or co-polymer that of high molecular weight. Plastics fitting this definition include, but are not limited to, polyolefins, polyesters, nylon, vinyl, acrylic, polycarbonates, polystyrene, and polyurethane.

The term "pressurized container" is defined herein as a container with contents, where the contents have a pressure of at least 5 PSI greater than atmospheric pressure at 25° C. The container can be fitted with a valve. Several types of materials can used to pressurize the container of the present invention. These materials include, but are not limited to, propellants and compressed gases. Propellants of the present invention include, but are not limited to, butane, isobutane, propane, dimethyl ether, 1,1difluoroethane and mixtures thereof. Compressed gases of the present invention include, but are not limited to, nitrogen ($N_2$), carbon dioxide ($CO_2$), and mixtures thereof.

The term "applicator" is defined herein includes a release system, including an actuating mechanism, fitted to the a pressurized container, wherein the release system is in fluid communication with the pressurized container, and wherein the actuating mechanism is designed to actuate the release system (comprising, for example, a valve) so as to allow the pressurized antiperspirant composition to flow out of the pressurized container directly onto the applicator's skin-contacting surface that is designed to distribute the required amount of the foaming antiperspirant composition onto a target surface (e.g. the underarm area of a user).

It is contemplated that the present invention may be practiced in many foaming consumer products including, but not limited to, antiperspirants, deodorants, hair styling mousse, shaving creams/gels, or drug products.

Applicator

An applicator 10 of the present invention, an exemplary embodiment of which is schematically shown in FIGS. 1-7A, has a longitudinal axis L and comprises a container 20 for storing, under pressure, the antiperspirant composition of the present. The container 20 can have a generally cylindrical configuration, and may comprise, in a horizontal cross-section (not shown): a circle, oval, rectangular, polygon, or any other suitable shape, symmetrical as well as asymmetrical.

The applicator 20 further comprises a release system 30 structured to facilitate discharge of the antiperspirant composition from the applicator 10. The release system 30 includes a valve 35 and an actuating mechanism 39 by which a consumer can actuate the valve 35 to dispense a desirable amount of the antiperspirant composition in the form of foam. Any suitable valve can be used in the present invention. The applicator 10 can be fitted with a continuous flow valve, or with a metered dose valve. In the instance of a continuous flow valve, the composition is continuously dispensed as the user actuates the discharge. This requires the user to determine visually when the appropriate amount of the composition is discharged to stop the process of dispensing. In the exemplary embodiment of FIG. 1, a conventional valve is located completely inside the container 20, but it is contemplated that other suitable designs may be employed, all of which are within the scope of the invention. While this approach is effective in delivering product to the application surface, it depends on the user to stop the actuation process at the optimal moment, and is thus highly variable in actual use. It may be beneficial to utilize a metered valve that would allow a user to discharge a small predetermined amount of the foaming antiperspirant composition during a single act of discharge, thereby minimizing the possibility for the user to over-dispense the product. This may be desirable in that it ensures that the user dispenses the ideal volume of the composition for each use and substantially reduces the likelihood of a user over-dispensing the composition, which can result in the product becoming messy or have poor application feel.

The actuating mechanism 39, which is in operative communication with the valve 35, extends through an opening in the container 20. While the button 39 is shown in FIG. 1 as a push button pivotally mounted on the container 20, it is to be understood that any other actuating mechanism can be used to engage and actuate the valve 35. For example, the actuating mechanism 39 may comprise, without limitation, a sliding (reciprocally moving) button, a rotating button, a spring-loaded device, a lever, none of which are shown in the drawings, but all of which are known to one skilled in the art and are within the scope of the present invention. The actuating means comprising electro-mechanical, magnetic, or sensory devices are also contemplated in the present invention.

The applicator 20 further comprises a skin-contacting surface 40 located at the top of the container 20. As the term suggests, the skin-contacting surface 40 is structured and configured to contact the desired skin area (typically an underarm area) of a user, thereby applying an effective amount of the foaming antiperspirant composition directly to the user's underarm area. By "direct" application, it is meant that a consumer need not use her or his hand to transfer the foaming antiperspirant composition from the applicator to the underarm area, but instead should use the applicator's skin-contacting surface to apply the desired amount of the foaming composition to the skin. This provides the important benefit of avoiding the need to remove the access of the composition from the consumer's hand and allows the user to avoid over-dosing, as well as and under-dosing, of the amount of the antiperspirant composition.

The skin-contacting surface 40 may have a variety of shapes, as long as those shapes are suitable for applying the antiperspirant foam to the underarm area of a consumer. For example, the skin-contacting surface 40 may be planar, concave, convex, concave-convex, irregular, or may comprise any combination thereof. Beneficially, the skin-contacting surface 40 may be constructed to comprise a flexible surface, to more easily conform to the underarm area of a consumer during application of the product. Various materials, such as thermoplastic elastomers, foams (having open and close cells), films, and other compressible and/or conformable materials can be used, alone or in combination with one another, to form a flexible or conformable surface. The skin-contacting surface can be slightly textured, to increase the overall surface area that is in contact with the foam being discharged.

The skin-contacting surface 40 is the surface onto which the antiperspirant composition is deposited during its discharge from the applicator. The antiperspirant composition is pressurized within the container 20 as a liquid, but becomes a foam as it is discharged onto the skin-contacting surface 40. One skilled in the art would appreciate that foam is a dispersion of gas bubbles in a continuous liquid medium. In the foaming antiperspirant composition of the present invention the antiperspirant active is suspended or dissolved in such a continuous liquid medium.

The skin-contacting surface 40 is structured and configured to retain from 0.2 to 2 grams of the foam thereon while greatly diminishing, if not completely eliminating, the possibility of dripping or sliding of the foam from the skin-contacting surface 40, even when the applicator 10 is angled, as typically happens during the use of the applicator by consumers. This unique benefit of the present invention allows one to apply a very limited amount (up to 2 gram) of the foaming antiperspirant composition to the skin in a uniform manner, while avoiding messiness.

Figure 6:
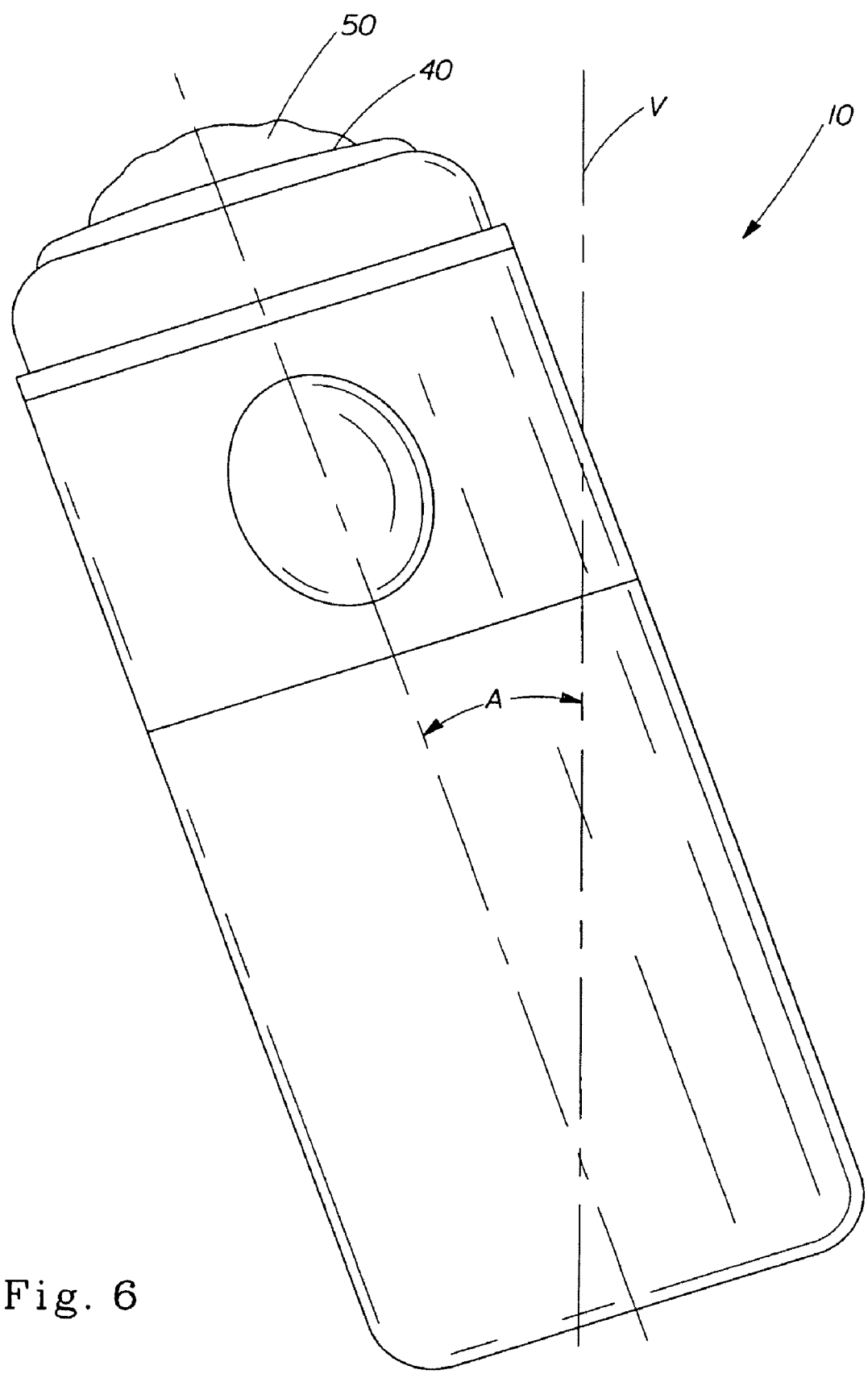
FIG. 6 is a schematic view of the applicator being inclined at an angle A relative to the gravity vector, the applicator having a portion of the foaming antiperspirant composition discharged onto the applicator's skin-contacting surface.
Figure 7:
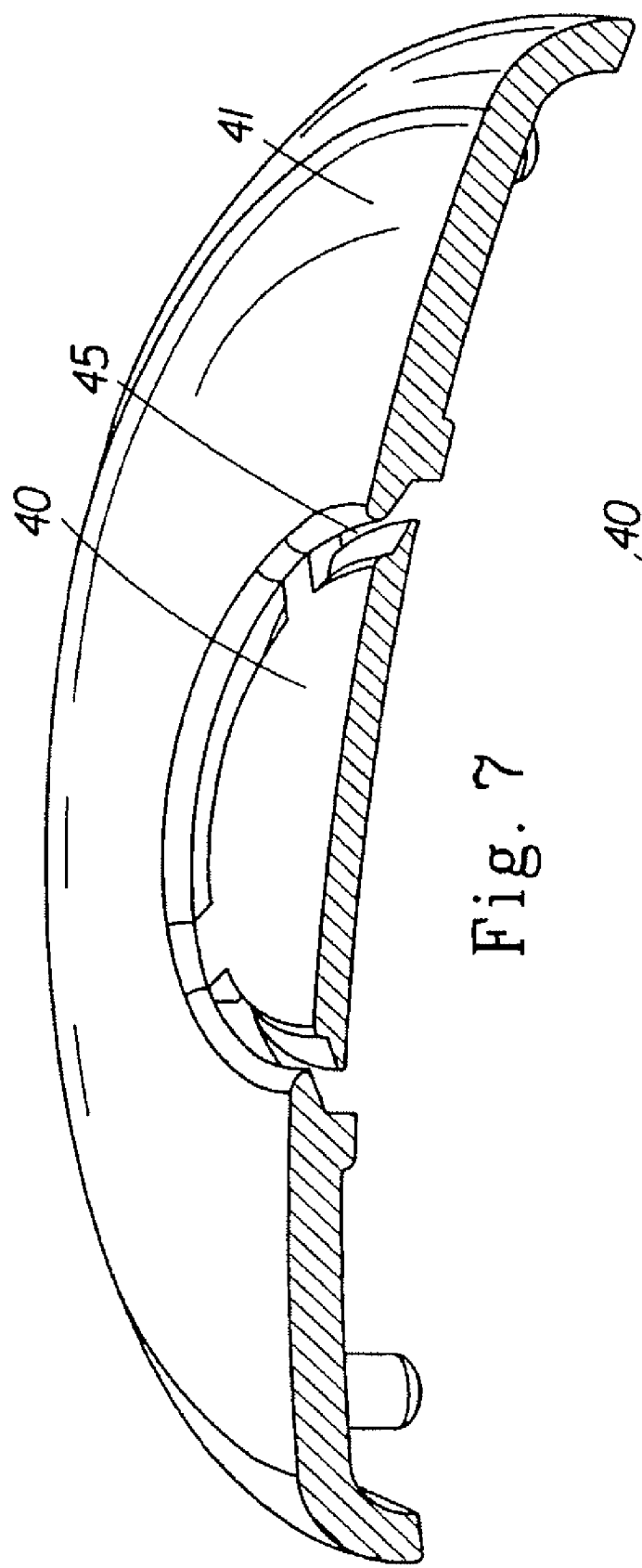
FIG. 7 is a schematic perspective view of a cut-off portion of another exemplary embodiment of the skin-contacting surface, which is structured to direct the flow of the antiperspirant composition away from the periphery of the skin-contacting surface.
Figure 7A:
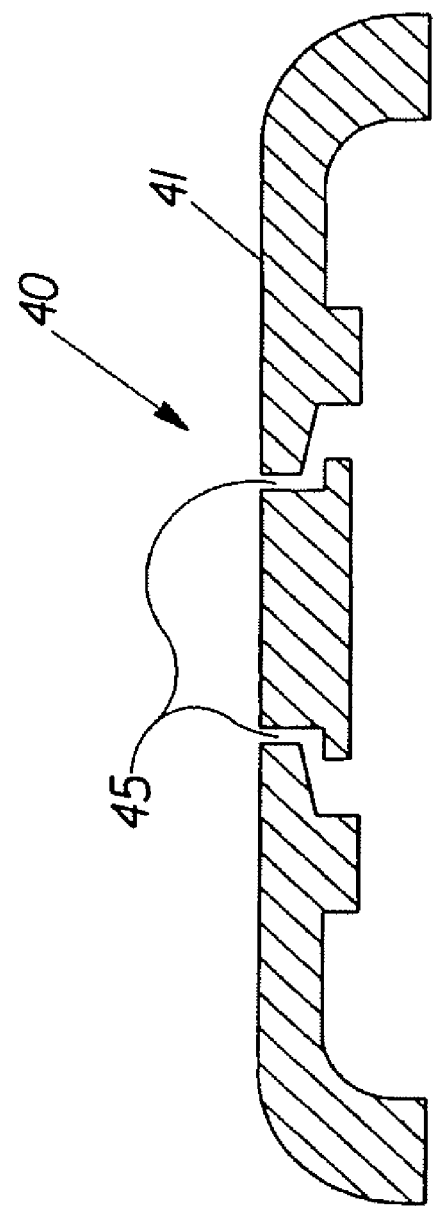
FIG. 7A is a schematic cross-sectional view of the exemplary embodiment of the skin-contacting surface shown in FIG. 7.

According to the present invention, the skin-contacting surface 40 of the applicator 10 is capable of receiving and retaining at least 0.2 gram, and more specifically at least 0.5 gram, of the foam 50 thereon such that the foam 50 is retained on the skin-contacting surface 40 for at least 2 seconds, and more specifically at least 5 seconds, when the applicator 10 is inclined so that the longitudinal axis L of the applicator 10 and a gravity force vector V form therebetween an angle A of about 15 degrees, more specifically about 45 degrees, and even more specifically about 90 degrees, FIG. 6.

Thus, the product of the present invention is designed to deliver the foam directly to the axilla (i.e., underarm area) in a convenient manner while the foam is maintained on the applicator's skin-contacting surface as the consumer moves the product to axilla to begin the application process. The present invention advantageously allows a consumer to discharge a required amount of the foaming antiperspirant composition onto the skin-contacting surface 40 of the applicator 10, and then to move the applicator 10 to an underarm area, while the foam is retained on the skin-contacting surface 40 without dripping or flowing down therefrom or otherwise causing messiness, even though the applicator 10 can be substantially inclined during its movement by the user.

The ability of the product to meet this requirement is tested by measuring the time during which the discharged onto the skin-contacting surface 40 portion of the foaming composition 50 that would provide antiperspirant efficacy is maintained without dripping or sliding off the skin-contacting surface 40 when the applicator 10 is positioned so that an angle A formed between the applicator's longitudinal axis L and the gravitational vector V comprises an angle between 0 degrees (when the applicator 10 is vertically-oriented) and 90 degrees (when the applicator 10 is horizontally oriented), for example, in three positions, wherein the angle A is 15 degrees, 45 degrees, and 90 degrees. One skilled in the art would appreciate that to conduct a test to determine such an attribute of the product of the present invention, one needs to first discharge the required amount of the foam 50 onto the skin-contacting surface 40 of the applicator 10 while the applicator 10 is oriented vertically, and then turn the applicator 10 to the desired position (e.g., 15 degrees, 45 degrees, or 90 degrees). The test may be conducted using visual observation as well as video recording.

The skin-contacting surface 40 can be beneficially and optionally provided with at least one depression 43 therein, FIG. 5A. In the embodiment of the applicator 10 shown in the drawings, the skin-contacting surface 40 comprises at least one exit orifice through which the antiperspirant composition in the form of foam is delivered onto the skin-contacting surface 40. In a particular embodiment best shown in FIGS. 4, 5, 5A, 7, and 7A, this at least one exit orifice comprises four slit-like curved channels 45 structured and configured to direct the flow of the antiperspirant composition towards the center of the skin-contacting surface 40 and away from the periphery 41 thereof.

Such a tangential (relative to the skin-contacting surface 40) direction of the flow of the antiperspirant composition, wherein several flows of the composition move towards one another and towards the center of the skin-contacting surface 40, encourages the foam 50 to remain, at least for a certain period of time, within a desired portion of the skin-contacting surface 40, and discourages the foam 40 from moving towards the periphery 41 of the skin-contacting surface 40, thereby reducing the possibility of dripping or sliding off the skin-contacting surface 40.

Figure 2:
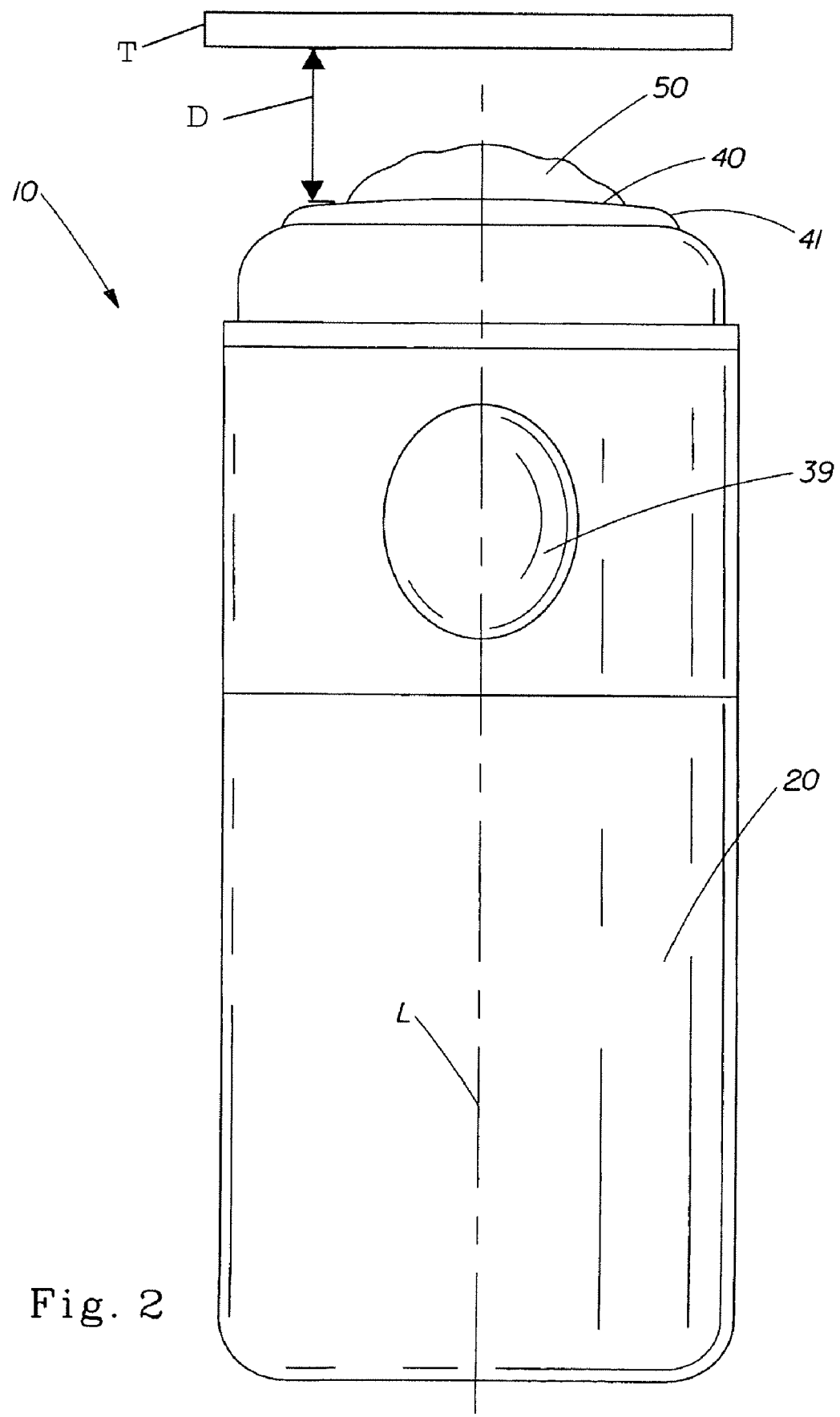
FIG. 2 is a schematic front view of the exemplary embodiment of the applicator of the present invention.
Figure 3:
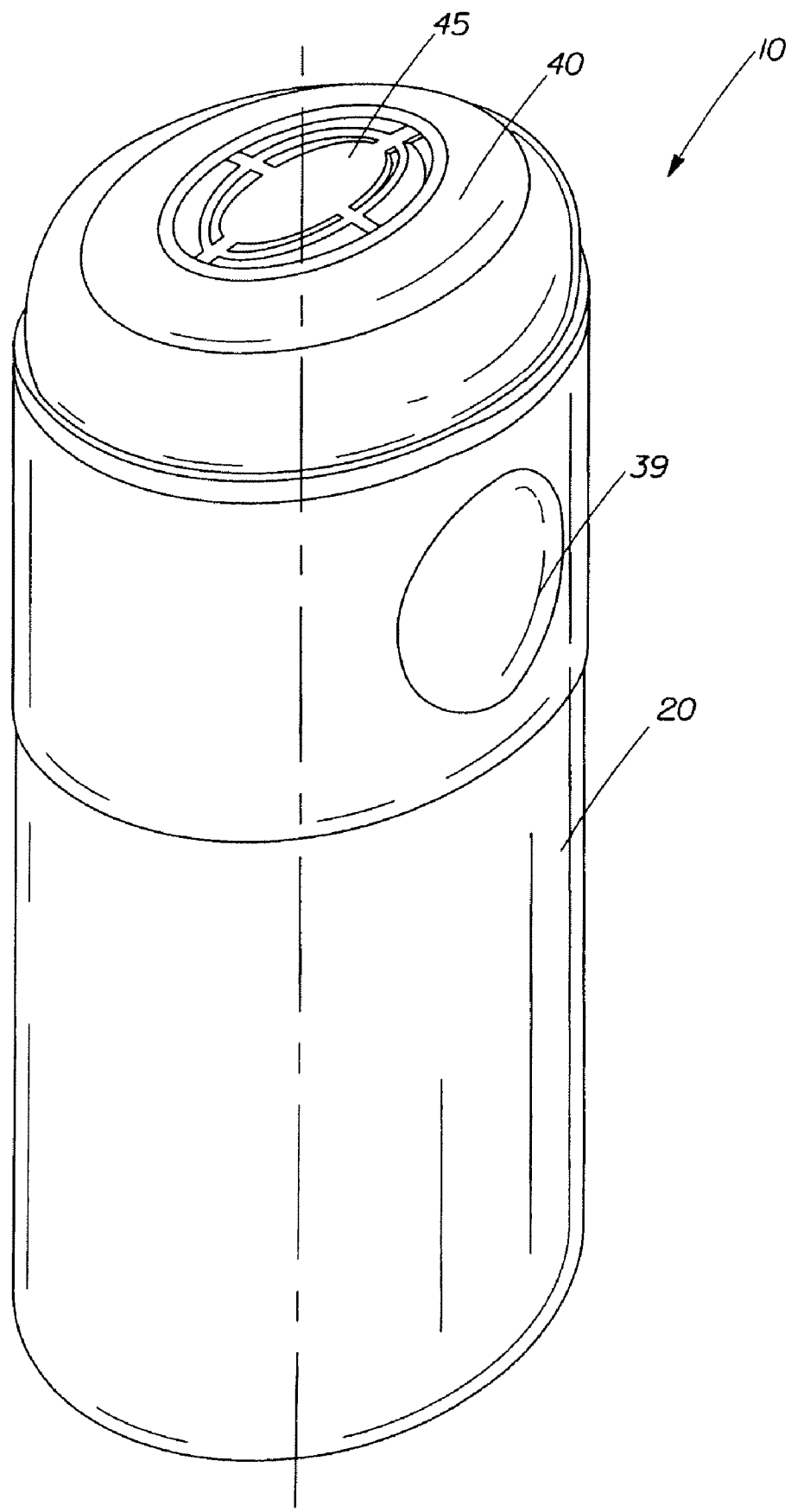
FIG. 3 is a schematic perspective view of the exemplary applicator shown in FIGS. 1 and 2.
Figure 4:
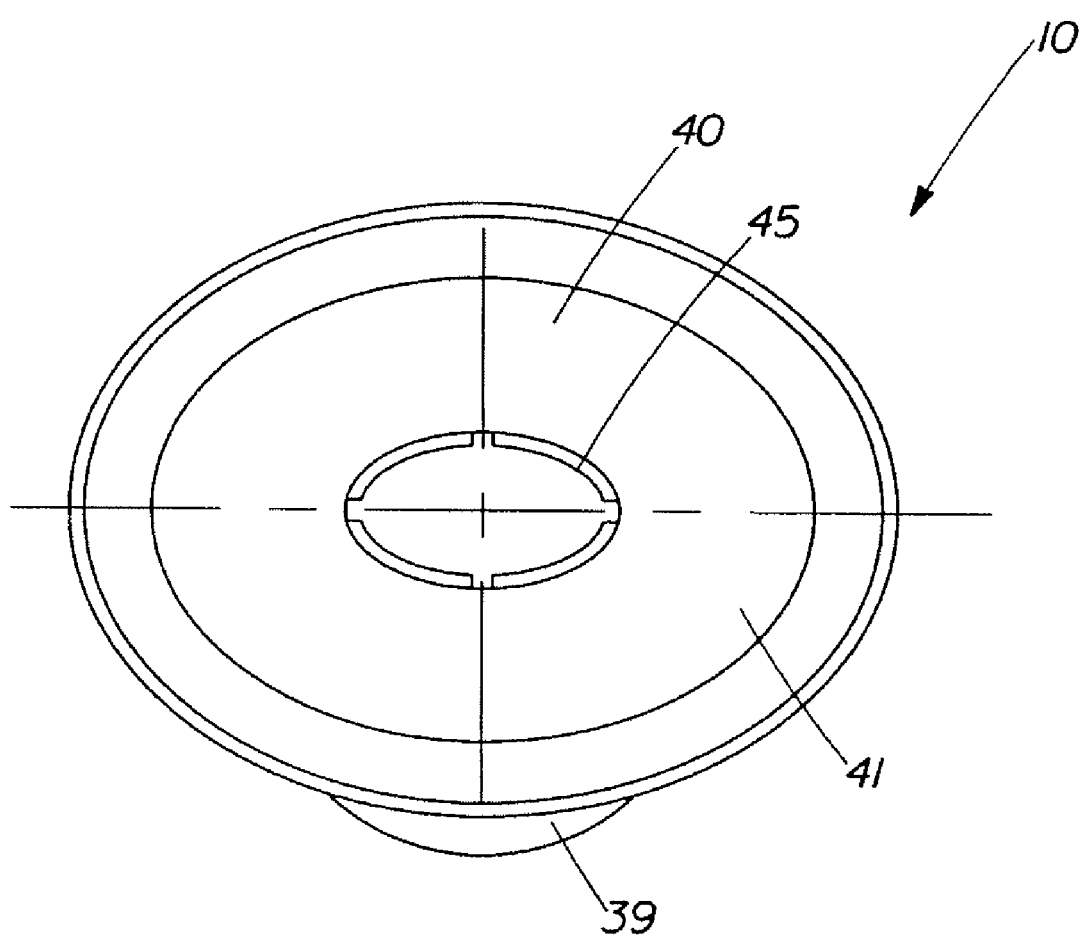
FIG. 4 is a schematic top view of the exemplary applicator shown in FIGS. 1-3, showing a plane view of a skin-contacting surface of the applicator.

In another aspect, the present invention provides the benefit of substantially preventing the antiperspirant composition from becoming airborne during discharge of the antiperspirant composition onto the skin-contacting surface 40. In accordance with the present invention, when a portion of about 0.5 gram of the antiperspirant composition including no less than 0.001 gram of at least one of an aluminum active or an aluminum-zirconium active or a mixture thereof is discharged onto the skin-contacting surface 40, less than 0.0004 gram, more specifically less than 0.0002 gram, and even more specifically less than 0.0001 gram, of the at least one of an aluminum or aluminum-zirconium active contained in the antiperspirant composition, is transferred to a target T (as shown in FIG. 2) having a diameter of at least 30 millimeters and positioned at a distance D (as shown in FIG. 2) of 35 millimeters directly above the skin-contacting surface 40 of the applicator 10. One skilled in the art would appreciate that the target area must be large enough to cover the entire projected area of the discharged foam 50 on the skin-contacting surface 40. Obviously, during the test the cap, if any, of the applicator is removed.

As used herein the term "discharge" and permutations thereof refer to a single act of dispensing of the antiperspirant composition onto the skin-contacting surface that typically lasts less than about 5 seconds, more specifically less than about 3 seconds, still more specifically less than about 2 seconds, and even more specifically about 1 second. Of course, in the instance of a metered-dose valve, some consumers may desire to actuate the valve more than once to discharge the desired amount of the composition.

The release system 30 may beneficially include a structure that would effectively reduce a velocity of the antiperspirant composition and direct its flow in the desired direction prior to dispensing onto the skin-contacting surface 40. For example, a flow diverter 36, FIG. 1, located below the skin-contacting surface 40, alone or in combination with an opposite side of the skin-contacting surface 40, can be used to direct the flow of the antiperspirant composition from a direction substantially perpendicular to the skin-contacting surface 40, and away from the center thereof, and towards the channels 45 of the skin-contacting surface 40, FIGS. 5, 5A, 7, and 7A. The flow diverter 36 and/or the underside of the skin-contacting surface 40 may includes a grid of solid posts (not shown) designed to create a treacherous flow path for the foam product as it is channeled to the application surface.

The direction of the flow of the antiperspirant composition, as it reaches the skin-contacting surface 40 can be regulated to be tangential to this surface, thus reducing the velocity of the foaming composition and at the same time diverting its vector towards tangential direction relative to the skin-contacting surface 40, thereby minimizing the potential for the foam to become airborne. The flow rate of the composition can be regulated to minimize the overall velocity of the antiperspirant composition as it reaches the application surface, thereby reducing the energy available to cause the foam to become airborne. One skilled in the art will realize that the cross sectional area of the exit orifice through the skin-contacting surface 40 can be increased or decreased to influence the velocity of the foam as it reaches the skin-contacting surface 40, thereby enabling the flow to be slowed to a rate that does not cause the foam to become airborne. Also, providing a treacherous path for the foam to flow as it is channeled to the skin-contacting surface facilitates the uniformity of the flow, and minimizes the potential for isolated areas of the flow having relatively higher flow rates to "shoot" through the exit orifice, thus also reducing the potential for the foam to become airborne.

Further, we believe that the treacherous path causes a portion of the gaseous propellant to separate from the foam prior to reaching the application surface, since the propellant more readily separates as it is sheared against the obstructions formed by the treacherous path, and the gaseous propellant flows much faster than the foam component of the composition toward the skin-contacting surface. This causes the foam product to reduce the amount of solubilized propellant by the time it reaches the skin-contacting surface, and to lower the expansion energy to create velocity that may cause the foam to become airborne.

A method that can be used to determine if the foam antiperspirant composition is becoming airborne upon dispensing is provided herein below. A piece of Whatman-1 filter paper having a diameter of at least 30 millimeters is held at a distance of 35 millimeters above the discharge orifice of the vertically-oriented applicator 10. The release system 30 of the applicator 10 is then actuated to discharge a portion of the composition of about 0.5 gram. The test is repeated 10 times, each time using a separate piece of filter paper as described herein above. The filter papers are then analyzed by XRF (X-Ray Fluorescence), for example a Phillips PW-2404 XRF analyzer, for a product component contained therein, if any. For products with an aluminum-zirconium active, analysis of zirconium should be preferred. For products with an aluminum-only active, analysis of aluminum should be performed.

The following sample preparation method can be used. The sample of filter paper is placed product-side down in the XRF liquid cup having a bottom formed by a plastic film Spectrolene-6, available from VHG Labs of Manchester, NH. One hundred microliters of 2% nitric acid is then added (using a pipette, for example) into the cup on top of the filter paper so that the added nitric acid spreads all over the filter paper. This wets the filter paper and helps the filter paper to lie smoothly and evenly on the film. A calibration plot can then be made by adding a small amount of the antiperspirant active in its carrier liquid to unused sheets of the same type filter paper. This calibration plot can be used to determine method linearity and limit of detection. One skilled in the art would appreciate how to perform the calibration. In the actual test performed for an antiperspirant composition of the present invention comprising an aluminum-zirconium active, the calibration plot showed a correlation coefficient, $r^2$, of 0.9935, and a linear range of 0 gram to 0.0000285 grams of zirconium. The average standard deviation of all standards was 2.33%. The average recovery of soluble active solutions added to the filter paper was 101.34%. The Limit of Quantitation based on a signal-to-noise ratio (S/N) of 10 is 0.0000045 grams of zirconium. The Limit of Detection based on a S/N of 3 is 0.0000013 gram of zirconium.

It is recognized that there can be several methods to analyze the presence of aluminum or zirconium on the filter paper and that any method could be employed, provided it has a similar limit of detection and recovery as the method described herein.

Antiperspirant Composition

Although any foaming antiperspirant composition may be used in the present invention, it is appreciated that the product will comprise an antiperspirant active suitable for application to human skin, a carrier liquid for the active, a foam-stabilizing agent, and a propellant. The concentration of antiperspirant active in the composition should be sufficient to provide the finished antiperspirant composition with the desired perspiration wetness and odor control. The antiperspirant active and the foam-stabilizing agent are dissolved or dispersed in the foam's continuous liquid medium that comprises at least 5% of a silicone emollient. The product may also optionally contain cosmetic emollients, deodorant agents, fragrances, and skin health agents.

(A) Antiperspirant Active

Antiperspirant active concentrations in the pressurized antiperspirant compositions may range from about 0.1% to about 26%, more specifically from about 1% to about 20%, and even more specifically from about 2% to about 10%, by weight of the composition. All such weight percentages are calculated on an anhydrous metal salt basis exclusive of water and any complexing or buffering agent such as glycine, glycine salts, or other complexing or buffering agent.

The antiperspirant active for use in the antiperspirant compositions of the present invention include any compound, composition or other material having antiperspirant activity. Antiperspirant actives may include astringent metallic salts, especially the inorganic and organic salts of aluminum, zirconium and zinc, as well as mixtures thereof. Salts such as aluminum halides, aluminum chlorohydrate, aluminum hydroxyhalides, zirconyl oxyhalides, zirconyl hydroxyhalides, and mixtures thereof can be used.

Aluminum salts for use in the antiperspirant compositions may beneficially include those that conform to the formula:

$$Al_2(OH)_aCl_b \cdot xH_2O$$

wherein a is from about 2 to about 5; the sum of a and b is about 6; x is from about 1 to about 6; and wherein a, b, and x may have non-integer values. More specifically, the aluminum chlorohydroxides referred to as "5/6 basic chlorohydroxide", wherein a=5, "2/3 basic chlorohydroxide" wherein a=4 and 1/3 basic chlorohydroxide" wherein a=2 may be used.

Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, and Gosling et al., issued Nov. 16, 1982, the disclosures of which are incorporated herein by reference. Mixtures of aluminum salts are described in British Patent Specification 1,347,950, Shin et al., published Feb. 27, 1974.

Zirconium salts for use in the antiperspirant compositions, especially in pressurized contact forms, may include those that conform to the formula:

$$ZrO(OH)_{2-a}Cl_a \cdot xH_2O,$$

wherein a is any number having a value of from 0 to about 2; x is from about 1 to about 7; and wherein a and x may both have non-integer values. Zirconium salts that additionally contain aluminum and glycine, commonly known as "ZAG" complexes, are believed to be beneficial. These ZAG complexes contain aluminum chlorohydroxide and zirconyl hydroxy chlorde conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978.

Antiperspirant actives for use in the compositions include aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlo+rohydrex polyethylene glycol complex, aluminum sulfate buffered, aluminum zirconium trichlorohydrex glycine, aluminum zirconium tetrachlorohydrex glycine, aluminum zirconium pentachlorohydrex glycine, aluminum zirconium octachlorohydrex glycine, zirconium trichlorohydrate, aluminum zirconium tetrachlorohydrate, aluminum zirconium pentachlorohydrate, aluminum zirconium octachlorohydrate, zirconium trichlorohydrex propylene glycol complex, aluminum zirconium tetrachlorohydrex propylene glycol complex, aluminum zirconium pentachlorohydrex propylene glycol complex, aluminum zirconium octachlorohydrex propylene glycol complex and combinations thereof.

Non-limiting examples of solubilized antiperspirant active for use in the pressurized antiperspirant compositions of the present invention, and methods of making the solubilized active, are described in U.S. Pat. No. 6,149,897 (Swaile); U.S. Pat. No. 6,126,928 (Swaile); and U.S. Pat. 5,968,489 (Swaile et al.). Other non-limiting examples of solubilized antiperspirant active and methods of making it are described in EP 0 404 533 (Smith et al.).

(B) Continuous Liquid Medium

The present invention can employ any continuous liquid medium to act as a carrier liquid that is capable of dissolving or dispersing the desired antiperspirant active. The continuous liquid medium of the composition of the present invention may comprise at least two immiscible liquids (example A, TABLE below). The continuous liquid medium of the foam antiperspirant composition may comprise only miscible liquids (examples B and C, TABLE below). In one embodiment, the continuous liquid medium comprises anhydrous solution (examples A-E, TABLE below). In another embodiment, the continuous liquid medium comprises an aqueous solution (example F). The continuous liquid medium of the foam antiperspirant composition may beneficially comprise a 1,2 diol having at least 4 carbon atoms (example A-E). The continuous liquid medium of the foam antiperspirant composition may also comprise a silicone emollient having a viscosity of less than about 500 cst. The present composition may utilize the foam-stabilizing agent that is a solid at a room temperature (example A-F).

Suitable carrier liquids that are capable of dissolving the antiperspirant active would include water as well as anhydrous carrier liquids. Suitable anhydrous carrier liquids would include selected liquid polyols for solubilizing for antiperspirant active material in the composition. The antiperspirant composition may comprise from about 1% to about 80%, more specifically from about 2% to about 60%, and even more specifically from about 3% to about 20%, by weight of the selected liquid polyols.

The liquid polyols for use in the foaming antiperspirant composition of the present invention are selected to have at least 4 carbon atoms and adjacent hydroxy-substituted carbon atoms at the α and β positions of the liquid polyol. Liquid polyols for use in the compositions may have the formula:

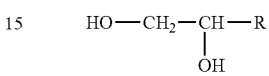

wherein R is an amide, ester, alkyl, ether or silicone-containing moiety, each moiety containing at least 1 carbon atom. The R group may be an alkyl or ether group, more specifically an alkyl group having from about 1 to about 10 carbon atoms, and even more specifically from about 2 to about 6 carbon atoms. The liquid polyols that have either 2 or 3 hydroxyl groups in total are believed to be beneficial.

The R group on the liquid polyol can be substituted or unsubstituted, branched or straight or cyclic, saturated or unsaturated. Non-limiting examples of suitable substituents include hydroxyl groups, amines, amides, esters, ethers, alkoxylate groups (e.g., ethoxylates, propoxylates, etc.) and so forth.

Non-limiting examples of suitable liquid polyols for use in the pressurized compositions of the present invention include; 1,2-butanediol; 1,2-pentanediol; 4-methyl-1,2-pentanediol; 2-methyl-1,2-pentanediol; 3,3-methyl-1,2-butanediol; 4-methyl-1,2-hexanediol; 1,2-heptanediol; 3-phenyl-1,2-propanediol; 1,2,6-hexanetriol; 1,2-hexanediol; 1,2,4-butanetriol; glycerine; and combinations thereof. Other suitable liquid polyols include glycerol ethers such as glycerol isopropyl ether; glycerol propyl ether; glycerol ethyl ether; glycerol methyl ether; glycerol butyl ether; glycerol isopentyl ether; diglycerol isopropyl ether; diglycerol isobutyl ether; diglycerol; triglycerol; triglycerol isopropyl ether; and combinations thereof. Still other suitable liquid polyols include acetic acid glycerol ester; propanoic acid glycerol ester; butanoic acid glycerol ester; 3-methyl butanoic acid glycerol ester; and 3-trimethylsily-1,2-propane diol; silicone-containing 1,2-diols such as those described in U.S. Pat. No. 5,969,172 (Nye); and combinations thereof.

Along with dissolving or dispersing the antiperspirant actives the carrier liquids in the continuous liquid medium should reduce the cosmetic negatives of stickiness and tackiness that can be associated with antiperspirant actives. This can be accomplished by adding a variety of cosmetic emollients to provide lubricity to the product. Suitable examples of these materials include low viscosity (less than 500 cps) hydrocarbon emollients and silicone emollients. Of these classes of materials silicone emollients may be especially beneficial due to their rapid spread rate on skin, dry feel, and ability to mitigate stickiness. The concentration of the silicone liquid in the composition may range from about 0.1% to about 50%, more specifically from about 1% to about 45%, and even more specifically greater than 5%, by weight of the antiperspirant composition.

Non limiting examples of suitable volatile silicones are described in Todd et al., "Volatile Silicone Fluids for Cosmetics", Cosmetics and Toiletries, 91:27-32 (1976), which descriptions are incorporated herein by reference. Cyclic silicones having from about 3 to about 7, more specifically from about 5 to about 6, silicon atoms may be beneficially used, including those that conform to the formula:

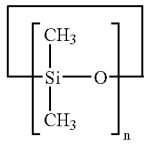

wherein n is from about 3 to about 7, more specifically from about 5 to about 6, and even more specifically 5. These volatile cyclic silicones generally have a viscosity value of less than about 10 centistokes as measured at 25° C. Suitable volatile silicones for use herein include, but are not limited to, Cyclomethicone D-5 (commercially available from G. E. Silicones); DC 1184, Dow Corning 344, and Dow Corning 345 (commercially available from Dow Corning Corp.); GE 7207, GE 7158 and Silicone Fluids SF-1202 and SF-1173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof. Cyclomethicone is believed to be especially beneficial among the volatile silicone liquids.

Non-limiting examples of non volatile silicone liquids for use in the antiperspirant compositions of the present invention include those that conform to either of the formulas:

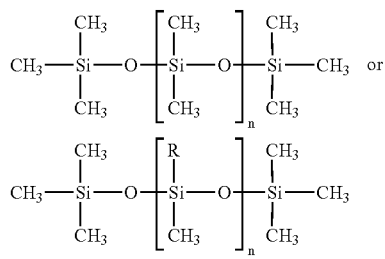

wherein n is greater than or equal to 1.

These linear silicone materials will generally have viscosity values of from about 10 centistokes to about 100,000 centistokes, specifically less than about 500 centistokes, more specifically from about 10 centistokes to about 200 centistokes, and even more specifically from about 10 centistokes to about 50 centistokes, as measured under ambient conditions. Non limiting examples of non-volatile, linear silicones suitable for use in the antiperspirant compositions include but are not limited to, Dow Corning 200, Rhodorsil Oils 70047 available from Rhone-Poulenc, Masil SF Fluid available from Mazer, Dow Corning 225, Dow Corning 1732, Dow Corning 5732, Dow Corning 5750 (available from Dow Corning Corp.); SF-96, SF-1066 and SF18(350) Silicone Fluids (available from G.E. Silicones); Velvasil and Viscasil (available from General Electric Co.); and Silicone L-45, Silicone L530, Silicone L-531 (available from Union Carbide), and Siloxane F-221 and Silicone Fluid SWS-101 (available from SWS Silicones).

Other silicone emollients that can be used as carrier liquids in the antiperspirant compositions of the present invention include modified or organofunctional silicone carriers such as polyalkylsiloxanes, polyalkyarylsiloxanes, cross-linked silicone elastomers, polyestersiloxanes, polyethersiloxane copolymers, polyfluorosiloxanes, polyaminosiloxanes, and combinations thereof. These modified silicone carriers are typically liquid under ambient conditions, and have a viscosity of less than about 100,000 centistokes, specifically less than about 500 centistokes, more specifically from about 1 centistokes to about 50 centistokes, and even more specifically from about 1 centistoke to about 20 centistokes. These modified silicone carriers are generally known in the chemical arts, some examples of which are described in 1 Cosmetics, Science and Technology 27-104 (M. Balsam and E. Sagarin ed. 1972); U.S. Pat. No. 4,202,879, issued to Shelton on May 13, 1980; U.S. Pat. No. 5,069,897, issued to Orr on Dec. 3, 1991; which descriptions are incorporated herein by reference. Beneficial organofunctional silicone carriers include DC5562, DC5560, and DC5529 from Dow Corning.

One skilled in the art will appreciate that including these silicone emollients in the product will create difficulty in creating a quality foam that is capable of being maintained on the skin contacting surface as these materials are well known in the art as defoaming agents.

C) Propellant

The propellant component of the pressurized antiperspirant composition of the present invention may contain dimethylether or a combination of dimethylether and any other known or otherwise suitable propellant for application to the skin, specifically a combination of dimethylether and a hydrocarbon propellant. The dimethylether or total propellant concentration in the pressurized antiperspirant compositions of the present invention ranges from about 5% to about 99%, more specifically from about 15% to about 90%, and even more specifically from about 30% to about 70%, by weight of the composition.

The hydrocarbon propellants suitable for use in the pressurized antiperspirant compositions include any hydrocarbon propellant known for or otherwise suitable for application to human skin, non limiting examples of which include propane, butane, pentane, isobutane, and combinations thereof Suitable examples of hydrocarbon propellants include A17, A32, A46, CAP40 and A108 propellants. These hydrocarbon propellants are generally in the form of liquefied gases when formulated into the antiperspirant compositions. The composition may comprise other propellants such as nitrous oxide, carbon dioxide, and halogenated hydrocarbons such as triclorofluoromethane, diclorodifluoromethane, diclorotetrafluoroethane trichlorotrifluoroethane, trichlorotetrafluoroethane, and monochlorodifluoromethane, and combinations thereof.

(D) Foam-Stabilizing Agent

Compositions of the current invention can employ a wide variety of foam-stabilizing agents (or simply foaming agents) that are well in known in the art. Foaming agents are known in the art as surfactants, foam boosters, foam stabilizers, and waxes. The foaming agent that is non-ionic may be beneficial to prevent interactions with the antiperspirant active. Anionic or cationic materials could be used provide that these interactions are minimized via some other manner. Suitable foaming agents include, but are not limited to: fatty alcohols, ethoxylated fatty alcohols, propoxylated fatty alcohols, amides of fatty alcohols. Suitable examples include, but are not limited to, stearyl alcohol, cetyl alcohol, behenyl alcohol, steareth-2, steareth-20, ceteareth-2 and ceteareth-20.

The TABLE below presents several examples (A-F) of the foaming antiperspirant composition of the present invention.

TABLE

| | A | B | C | D | E | F |
|---|---|---|---|---|---|---|
| Aluminum chlorohydrate In 1,2 hexanediol | 32 | 32 | | | | |
| Aluminum Zirconium Tetrachlorohydrate In 1,2 hexanediol | | | 32 | | 32 | |
| Aluminum chlorohydrate In 1,2 pentanediol | | | | 32 | | |
| Aluminum Zirconium Tetrachlorohydrate In water | | | | | | 35 |
| 1,2 Hexandiol | | | | | 17 | 10 |
| DC5562 | 32 | 32 | 32 | 16 | 5 | 10 |
| DC5529 | | | | 16 | | |
| Dimethicone | | 8 | | | | |
| Cyclopentasiloxane | 2 | | | 10 | | |
| Dimethyl ether | 10 | | | 10 | 20 | 20 |
| Butane | 10 | 34 | 31 | 10 | 20 | |
| Stearyl alcohol | 3 | | 4 | 3 | 5 | |
| Cetyl alcohol | 2 | | | 2 | | |
| Behenyl alcohol | | 1 | | | | |
| Steareth 20 | | | | | | 3 |
| Steareth 2 | | | | | | 2 |
| Water | | | | | | 19 |
| Fragrance | 1 | 1 | 1 | 1 | 1 | 1 |

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An antiperspirant product comprising:
    (a) an antiperspirant composition comprising an antiperspirant active; and
    (b) an applicator for storing and discharging the antiperspirant composition, the applicator having a longitudinal axis and comprising
        a release system structured to facilitate discharge of the antiperspirant composition such that the antiperspirant composition discharges as a portion of a foam comprising a dispersion of gas bubbles in a continuous liquid medium comprising the antiperspirant active that is suspended or dissolved therein, and
        a skin-contacting surface structured to receive and retain thereon the portion of the foam that is at least 0.2 gram such that the portion of the foam is retained on the skin-contacting surface for at least 2 seconds when the applicator is inclined so that the longitudinal axis of the applicator and a gravity force vector form an angle of about 15 degrees therebetween, the skin-contacting surface being configured to apply an effective amount of the foam directly to an underarm area of a consumer,
    wherein the antiperspirant composition is clear, transforms into an opaque foam upon transfer to the skin-contacting surface, and then returns to clear when rubbed against the underarm.

2. The product of claim 1, wherein the skin-contacting surface is configured to receive and retain thereon the portion of the foam that is at least 0.2 gram such that the portion of the foam is retained on the skin-contacting surface for at least 2 seconds when the applicator is inclined so that the longitudinal axis of the applicator and a gravity force vector form an angle of about 45 degrees therebetween.

3. The product of claim 1, wherein the skin-contacting surface is configured to receive and retain thereon the portion of the foam that is at least 0.2 gram such that the portion of the foam is retained on the skin-contacting surface for at least 2 seconds when the applicator is inclined so that the longitudinal axis of the applicator and a gravity force vector form an angle of about 90 degrees therebetween.

4. The product of claim 1, wherein the skin-contacting surface is configured to receive and retain thereon the portion of the foam that is at least 0.2 gram such that the portion of the foam is retained on the skin-contacting surface for at least 5 seconds when the applicator is inclined so that the longitudinal axis of the applicator and a gravity force vector form an angle of about 15 degrees therebetween.

5. The product of claim 1, wherein the skin-contacting surface is configured to receive and retain thereon the portion of the foam that is at least 0.2 gram such that the portion of the foam is retained on the skin-contacting surface for at least 5 seconds when the applicator is inclined so that the longitudinal axis of the applicator and a gravity force vector form an angle of about 45 degrees therebetween.

6. The product of claim 1, wherein the skin-contacting surface is configured to receive and retain thereon the portion of the foam that is at least 0.2 gram such that the portion of the foam is retained on the skin-contacting surface for at least 5 seconds when the applicator is inclined so that the longitudinal axis of the applicator and a gravity force vector form an angle of about 90 degrees therebetween.

7. The product of claim 1, wherein the skin-contacting surface is configured to receive and retain thereon the portion of the foam that is at least 0.5 gram such that the portion of the foam is retained on the skin-contacting surface for at least 2 seconds when the applicator is inclined so that the longitudinal axis of the applicator and a gravity force vector form an angle of about 15 degrees therebetween.

8. The product of claim 1, wherein the skin-contacting surface is configured to receive and retain thereon the portion of the foam that is at least 0.5 gram such that the portion of the foam is retained on the skin-contacting surface for at least 2 seconds when the applicator is inclined so that the longitudinal axis of the applicator and a gravity force vector form an angle of about 45 degrees therebetween.

9. The product of claim 1, wherein the skin-contacting surface is configured to receive and retain thereon the portion of the foam that is at least 0.5 gram such that the portion of the foam is retained on the skin-contacting surface for at least 2 seconds when the applicator is inclined so that the longitudinal axis of the applicator and a gravity force vector form an angle of about 90 degrees therebetween.

10. The product of claim 1, wherein the skin-contacting surface is configured to receive and retain thereon the portion of the foam that is at least 0.5 gram such that the portion of the foam is retained on the skin-contacting surface for at least 5 seconds when the applicator is inclined so that the longitudinal axis of the applicator and a gravity force vector form an angle of about 15 degrees therebetween.

11. The product of claim 1, wherein the skin-contacting surface is configured to receive and retain thereon the portion of the foam that is at least 0.5 gram such that the portion of the foam is retained on the skin-contacting surface for at least 5 seconds when the applicator is inclined so that the longitudinal axis of the applicator and a gravity force vector form an angle of about 45 degrees therebetween.

12. The product of claim 1, wherein the skin-contacting surface is generally convex.

13. The product of claim 1, wherein the skin-contacting surface comprises at least one depression therein.

14. The product of claim 1, wherein the skin-contacting surface is structured to direct the antiperspirant composition being discharged away from a periphery of the skin-contacting surface.

15. The product of claim 1, wherein the skin-contacting surface comprises a flexible material.

16. The product of claim 1, wherein the antiperspirant composition is clear prior to being foamed, becomes opaque when foamed, and then returns to clear upon rubbing against an underarm.

17. An antiperspirant product comprising:
(a) an antiperspirant composition comprising an antiperspirant active comprising salts of aluminum or zirconium or a mixture thereof; and
(b) an applicator for storing and discharging the antiperspirant composition, the applicator comprising
a skin-contacting surface having a discharge orifice therethrough and a periphery thereof, and
a release system structured to facilitate discharge of the antiperspirant composition onto the skin-contacting surface such that the antiperspirant composition discharges through the discharge orifice as a foam comprising the antiperspirant active suspended or dissolved in a continuous liquid medium,
wherein the applicator is structured to prevent the antiperspirant composition from becoming airborne during discharge of the antiperspirant composition onto the skin-contacting surface, such that when a portion of about 0.5 gram of the antiperspirant composition including no less than 0.001 gram of at least one of an aluminum active or an aluminum-zirconium active or a mixture thereof is discharged onto the skin-contacting surface, less than 0.0004 gram of the at least one of the aluminum active or aluminum-zirconium active or a mixture thereof is transferred to a target having a diameter of 30 millimeters and positioned at a distance of 35 millimeters directly above the skin-contacting surface, and
wherein the antiperspirant composition is clear, transforms into an opaque foam upon transfer to the applicator surface, and then returns to clear when rubbed against the underarm.

18. The product of claim 17, wherein when a portion of about 0.5 gram of the antiperspirant composition including no less than 0.001 gram of at least one of aluminum or zirconium is discharged onto the skin-contacting surface, less than 0.0002 gram of the at least one of aluminum or zirconium active is transferred to a target having a diameter of 30 millimeters and positioned at a distance of 35 millimeters directly above the skin-contacting surface.

19. The product of claim 17, wherein when a portion of about 0.5 gram of the antiperspirant composition including no less than 0.001 gram of at least one of aluminum or zirconium is discharged onto the skin-contacting surface, less than 0.0001 gram of the at least one of aluminum or zirconium active is transferred to a target having a diameter of 30 millimeters and positioned at a distance of 35 millimeters directly above the skin-contacting surface.

20. The product of claim 17, further comprising a structure located below the skin-contacting surface configured to reduce a velocity of the antiperspirant composition being discharged.

21. The product of claim 17, wherein the discharge orifice of the skin-contacting surface comprises at least one channel structured to direct the antiperspirant composition being discharged away from the periphery of the skin-contacting surface.

22. The product of claim 17, wherein the applicator is structured to direct the flow of the antiperspirant composition being discharged tangentially relative to the skin-contacting surface.

23. The product of claim 17, wherein the antiperspirant composition is clear prior to being foamed, becomes opaque when foamed, and then returns to clear upon rubbing against an underarm.

24. A foam antiperspirant product, comprising:
i) a packaging comprising a container and an applicator surface; and
ii) a foaming antiperspirant composition disposed in the container, the foaming antiperspirant composition comprising a dispersed gas phase in a continuous liquid medium, and comprising the following components:
(a) an antiperspirant active;
(b) a foam-stabilizing agent; and
(c) a propellant,
wherein the antiperspirant active and the foam-stabilizing agent are dissolved or dispersed in the continuous liquid medium; wherein the continuous liquid medium comprises a silicone emollient; and
wherein the foaming antiperspirant composition is clear when disposed in the container, transforms into an opaque foam upon transfer to the applicator surface, and then returns to clear when rubbed against the underarm.

25. The foaming antiperspirant product of claim 24, comprising at least 5% of a silicone emollient.

26. The foaming antiperspirant product of claim 24, wherein the continuous liquid medium comprises at least two immiscible liquids.

27. The foam antiperspirant composition of claim 24, wherein the continuous liquid medium comprises only miscible liquids.

28. The foaming antiperspirant product of claim 24, wherein the continuous liquid medium comprises anhydrous solution.

29. The foaming antiperspirant product of claim 24, wherein the continuous liquid medium comprises an aqueous solution.

30. The foaming antiperspirant product of claim 24, wherein the continuous liquid medium comprises a 1,2 diol having at least 4 carbon atoms.

31. The foaming antiperspirant product of claim 24, wherein the continuous liquid medium comprises a silicone emollient having a viscosity of less than about 500 cst.

32. The foaming antiperspirant product of claim 24, wherein the foam-stabilizing agent is a solid at a room temperature.

33. The foaming antiperspirant product of claim 24, wherein the container is a clear container.

34. The foaming antiperspirant product of claim 24, wherein the container is a clear plastic container.

35. An antiperspirant product comprising:
(a) an antiperspirant composition comprising an antiperspirant active; and
(b) an applicator for storing and discharging the antiperspirant composition, the applicator having a longitudinal axis and comprising:
a release system structured to facilitate discharge of the antiperspirant composition such that the antiperspirant composition discharges as a portion of a foam comprising a dispersion of gas bubbles in a continuous liquid medium comprising the antiperspirant active that is suspended or dissolved therein; and a skin-contacting surface structured to receive and retain thereon the portion of the foam, the skin-contacting surface comprising at least one exit orifice that is configured to direct flow of the antiperspirant composition in a tangential direction relative to the skin-contacting surface.

36. The product of claim 35, wherein the at least one exit orifice comprises a slit comprising a radially inwardly angled surface.

37. The product of claim 35, wherein the at least one exit orifice is structured to direct the flow of the antiperspirant composition towards the center of the skin-contacting surface and away from the periphery of the skin-contacting surface.

38. The product of claim 35, wherein the at least one exit orifice comprises opposing channels that direct flows of the antiperspirant composition towards one another and towards the center of the skin-contacting surface.

39. The product of claim 35, wherein the skin-contacting surface is configured to receive and retain thereon the portion of the foam that is at least 0.2 gram such that the portion of the foam is retained on the skin-contacting surface for at least 2 seconds when the applicator is inclined so that the longitudinal axis of the applicator and a gravity force vector form an angle of about 45 degrees therebetween.

40. The product of claim 35, wherein the applicator is structured to prevent the antiperspirant composition from becoming airborne during discharge of the antiperspirant composition onto the skin-contacting surface, such that when a portion of about 0.5 gram of the antiperspirant composition including no less than 0.001 gram of at least one of an aluminum active or an aluminum-zirconium active or a mixture thereof is discharged onto the skin-contacting surface, less than 0.0004 gram of the at least one of the aluminum active or aluminum-zirconium active or a mixture thereof is transferred to a target having a diameter of 30 millimeters and positioned at a distance of 35 millimeters directly above the skin-contacting surface.

* * * * *